United States Patent
Nakayama et al.

(10) Patent No.: US 10,880,301 B2
(45) Date of Patent: *Dec. 29, 2020

(54) IDENTIFICATION DEVICE AND IDENTIFICATION METHOD

(71) Applicant: PANASONIC INTELLECTUAL PROPERTY MANAGEMENT CO., LTD., Osaka (JP)

(72) Inventors: Takeshi Nakayama, Hyogo (JP); Shoichi Iizuka, Osaka (JP); Naoki Honma, Iwate (JP); Dai Sasakawa, Iwate (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 281 days.

This patent is subject to a terminal disclaimer.

(21) Appl. No.: 16/196,853

(22) Filed: Nov. 20, 2018

(65) Prior Publication Data
US 2019/0158494 A1    May 23, 2019

(30) Foreign Application Priority Data

Nov. 21, 2017 (JP) .................. 2017-223430
May 31, 2018 (JP) .................. 2018-105032

(51) Int. Cl.
*H04L 29/06* (2006.01)
*G06F 17/15* (2006.01)
(Continued)

(52) U.S. Cl.
CPC ........ *H04L 63/0861* (2013.01); *A61B 5/0536* (2013.01); *A61B 5/117* (2013.01);
(Continued)

(58) Field of Classification Search
CPC .................. H04L 63/0861; A61B 5/0536
See application file for complete search history.

(56) References Cited

U.S. PATENT DOCUMENTS

| | | | |
|---|---|---|---|
| 10,413,229 B2* | 9/2019 | Nakayama | A61B 5/18 |
| 10,561,358 B2* | 2/2020 | Nakayama | A61B 5/18 |

(Continued)

FOREIGN PATENT DOCUMENTS

| | | |
|---|---|---|
| JP | 2005-314847 | 11/2005 |
| JP | 2007-325621 | 12/2007 |

(Continued)

OTHER PUBLICATIONS

An Extended European Search Report dated Apr. 29, 2019 issued in European patent application No. 18206538.3.

(Continued)

*Primary Examiner* — Shin-Hon (Eric) Chen
(74) *Attorney, Agent, or Firm* — Greenblum & Bernstein, P.L.C.

(57) ABSTRACT

An identification device includes: M transmission antenna elements each of which transmits a first transmission signal to a predetermined area including a first living body; N receivers disposed surrounding the predetermined area, and each including a reception antenna element and receiving, using the reception antenna element, a first reception signal including a reflection signal obtained as a result of the first transmission signal being reflected by the first living body, during a predetermined period; a memory storing teacher signals which are M×N second reception signals obtained about a second living body; and a circuit which calculates a plurality of correlation coefficients from the teacher signals and M×N first reception signals obtained as a result of each of the N receivers receiving the first reception signal, performs biometric authentication of the first living body, and identifies the first living body and the second living body as identical.

6 Claims, 10 Drawing Sheets

(51) Int. Cl.
*H04L 25/06* (2006.01)
*G06K 9/00* (2006.01)
*A61B 5/117* (2016.01)
*A61B 5/00* (2006.01)
*G06F 21/32* (2013.01)

(52) U.S. Cl.
CPC ............ *A61B 5/7264* (2013.01); *G06F 17/15* (2013.01); *G06F 21/32* (2013.01); *G06K 9/00536* (2013.01); *G06K 9/00906* (2013.01); *H04L 25/061* (2013.01)

(56) References Cited

U.S. PATENT DOCUMENTS

| | | | | |
|---|---|---|---|---|
| 2010/0152600 | A1* | 6/2010 | Droitcour | A61B 5/1114 600/534 |
| 2013/0093616 | A1* | 4/2013 | Jeon | G01S 13/66 342/118 |
| 2013/0113653 | A1* | 5/2013 | Kishigami | G01S 7/4021 342/189 |
| 2016/0042169 | A1* | 2/2016 | Polehn | G06F 21/35 726/20 |
| 2017/0351848 | A1* | 12/2017 | Bakish | G06F 21/32 |
| 2019/0011534 | A1* | 1/2019 | Trotta | G06F 21/32 |

FOREIGN PATENT DOCUMENTS

| | | |
|---|---|---|
| JP | 2009-055997 | 3/2009 |
| JP | 2015-042293 | 3/2015 |
| JP | 2016-202516 | 12/2016 |
| WO | 2017/156487 | 9/2017 |
| WO | WO-2017156487 A1 * | 9/2017 ............... G07C 9/00 |

OTHER PUBLICATIONS

Sasakawa et al., "Human Identification Using MIMO Array", Journal of Latex Class Files, vol. 14, No. 8, Aug. 2015, pp. 1-7.

* cited by examiner

IDENTIFICATION DEVICE AND IDENTIFICATION METHOD

CROSS REFERENCE TO RELATED APPLICATION

This application claims the benefit of priority of Japanese Patent Application Number 2017-223430 filed on Nov. 21, 2017, and Japanese Patent Application Number 2018-105032 filed on May 31, 2018 the entire content of which is hereby incorporated by reference.

BACKGROUND

1. Technical Field

The present disclosure relates to an identification device and method for identifying a living body by emitting a radio signal to the living body and receiving a reflection signal therefrom.

2. Description of the Related Art

There are known techniques for identifying a living body by emitting a radio signal to the living body and receiving a reflection signal therefrom (for example, Japanese Unexamined Patent Application Publications No. 2015-042293 and No. 2009-055997). Japanese Unexamined Patent Application Publication No. 2015-042293 discloses a device which emits an electromagnetic wave toward a driver of a vehicle and extracting, from a reflection wave therefrom, heartbeat and heart sound signals to identify the driver him or herself. Japanese Unexamined Patent Application Publication No. 2009-055997 discloses a method for measuring the heart rate of a subject using a plurality of transmitters and receivers for a driver of a vehicle.

Furthermore, for example, Japanese Unexamined Patent Application Publication No. 2007-325621 discloses a 360-degree radiation pattern measurement device which uses more than one antenna for a subject.

SUMMARY

There are many instances in biometric identification using an electromagnetic wave where teacher data and measurement data obtained by measuring a subject are compared to perform the biometric identification.

However, if data of the subject is not included in the teacher data, teacher data closest to the data of the subject is recognized as the data of the subject him or herself, and thus a different person is erroneously accepted, which is problematic.

The present disclosure has been conceived in view of the above-described circumstances and has an object to provide an identification device and method in which an equal error rate (EER) which is a balance point between a false acceptance rate (FAR) and a false rejection rate (FRR) is reduced.

In order to achieve the aforementioned object, an identification device according to one embodiment of the present disclosure includes: M transmission antenna elements each of which transmits a first transmission signal to a predetermined area including a first living body, M being an integer greater than or equal to 1; N receivers disposed surrounding the predetermined area, each of the N receivers including a reception antenna element and receiving a first reception signal using the reception antenna element during a predetermined period, N being an integer greater than or equal to 3, the first reception signal including a reflection signal obtained as a result of the first transmission signal being reflected by the first living body; a memory in which teacher signals are stored, the teacher signals being M×N second reception signals obtained as a result of the N receivers receiving, in advance, second reception signals including reflection signals obtained as a result of second transmission signals being transmitted from the M transmission antenna elements to a second living body and reflected by the second living body; and a circuit which calculates a plurality of correlation coefficients from the teacher signals and M×N first reception signals obtained as a result of each of the N receivers receiving the first reception signal, performs biometric authentication of the first living body according to whether or not a maximum value of the plurality of correlation coefficients calculated exceeds a threshold, and when the biometric authentication of the first living body is to be performed, identifies by a predetermined method the first living body and the second living body as identical.

Note that these general and specific aspects may be implemented using a system, a method, an integrated circuit, a computer program, or a computer-readable recording medium such as a compact disc read-only memory (CD-ROM), or any combination of systems, methods, integrated circuits, computer programs, or recording media.

With the identification device according to the present disclosure, the equal error rate of biometric identification is reduced.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE EMBODIMENT

Figure 1:
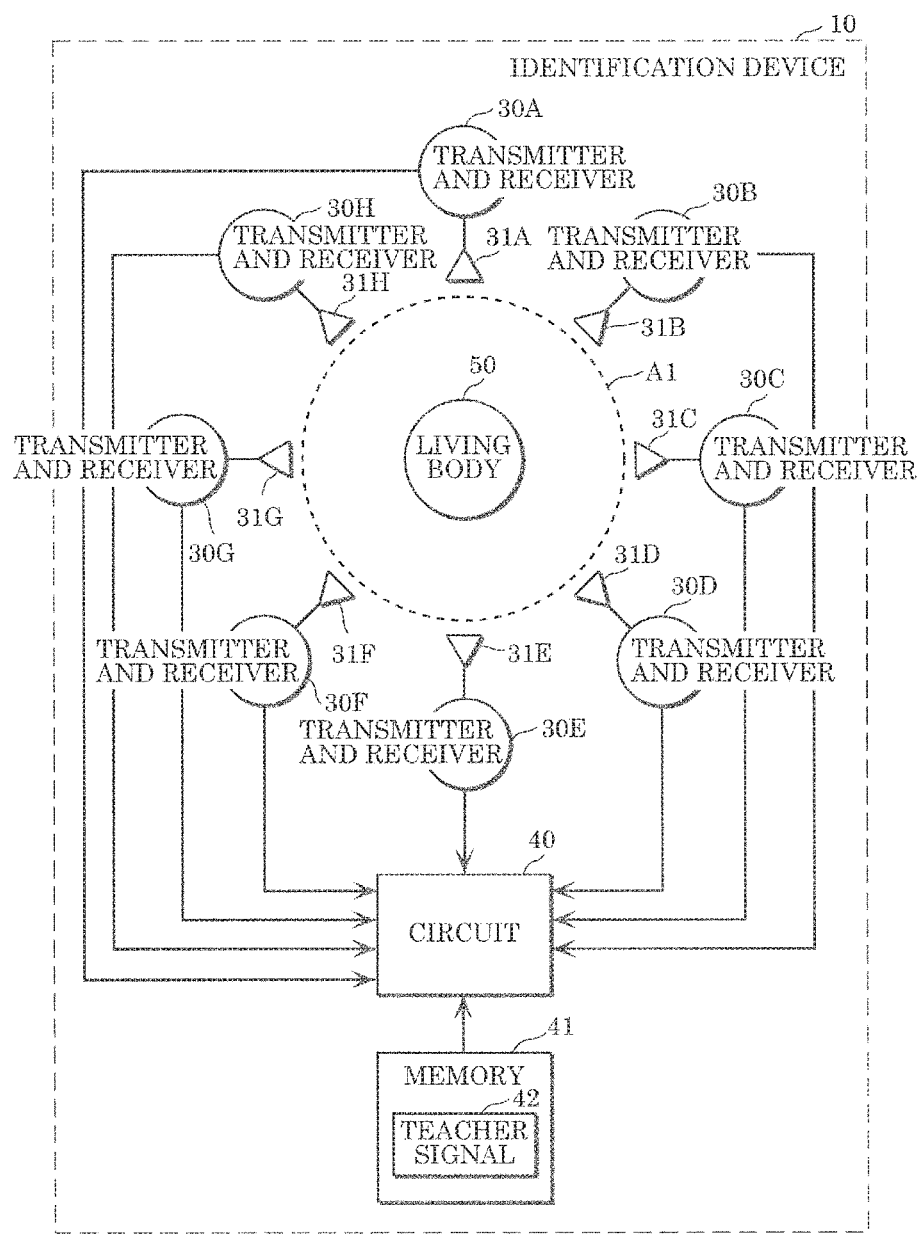
FIG. 1 is a configuration diagram illustrating an example of the configuration of an identification device according to an embodiment.

Underlying Knowledge Forming Basis of the Present Disclosure

In Japanese Unexamined Patent Application Publications No. 2015-042293 and No. 2009-055997, an electromagnetic wave is emitted to a person sitting in a driver seat of a vehicle and a reflection wave from the person is measured. Subsequently, calculation is performed on the measurement result to measure heartbeat or heart sounds, and a time correlation of the measured heartbeat or heart sounds is obtained; in this way, biometric identification is implemented. However, as mentioned above, there is the problem that if data of the subject is not included in the teacher data, teacher data closest to the data of the subject is recognized as the data of the subject him or herself, and thus a different person is erroneously accepted.

There is a relationship in which when the threshold used for determination in such biometric identification is lowered, the false rejection rate (FRR) is reduced and the false acceptance rate (FAR) increases. On the other hand, there is a relationship in which when the threshold is raised, the false rejection rate increases and the false acceptance rate is reduced. This means that there is no point in reducing the false acceptance rate (FAR) alone; it is necessary to reduce both the false rejection rate (FRR) and the false acceptance rate (FAR). In other words, there is a demand for reduction in an equal error rate at which the false rejection rate (FRR) and the false acceptance rate (FAR) are equal (which is a balance point therebetween).

The inventors have continuously studied this problem and found the following in order to reduce the equal error rate (EER) of an identification device which identifies a living body. Specifically, antenna elements are installed around a living body to be identified, transmission waves are transmitted thereto in various directions, and reflection waves and scattered waves are received in various directions so that a reception signal capturing a larger number of features of the living body is obtained. Subsequently, a plurality of correlation coefficients between the reception signal and teacher data are calculated; the inventors found that in this way, whether or not the living body, i.e., a measurement target, is included in the teacher data can be accurately identified.

More specifically, in order to achieve the aforementioned object, an identification device according to one aspect of the present disclosure includes: M transmission antenna elements each of which transmits a first transmission signal to a predetermined area including a first living body, M being an integer greater than or equal to 1; N receivers disposed surrounding the predetermined area, each of the N receivers including a reception antenna element and receiving a first reception signal using the reception antenna element during a predetermined period, N being an integer greater than or equal to 3, the first reception signal including a reflection signal obtained as a result of the first transmission signal being reflected by the first living body; a memory in which teacher signals are stored, the teacher signals being M×N second reception signals obtained as a result of the N receivers receiving, in advance, second reception signals including reflection signals obtained as a result of second transmission signals being transmitted from the M transmission antenna elements to a second living body and reflected by the second living body; and a circuit which calculates a plurality of correlation coefficients from the teacher signals and M×N first reception signals obtained as a result of each of the N receivers receiving the first reception signal, performs biometric authentication of the first living body according to whether or not a maximum value of the plurality of correlation coefficients calculated exceeds a threshold, and when the biometric authentication of the first living body is to be performed, identifies by a predetermined method the first living body and the second living body as identical.

With this, a plurality of correlation coefficients can be calculated from teacher signals and first reception signals which are measurement signals obtained from reception antenna elements installed around a first living body. Subsequently, according to whether or not the maximum value of the plurality of correlation coefficients exceeds a threshold, the first living body and a second living body included in teacher data are identified as identical; in this way, the biometric authentication can be performed. Therefore, it is possible to reduce the occurrences of erroneous acceptance of a different person as a subject him or herself when the first living body is not included in the teacher data, enabling a reduction in the equal error rate (EER).

For example, the circuit performs the biometric authentication of the first living body when the maximum value of the plurality of correlation coefficients calculated exceeds the threshold, and refrains from performing the biometric authentication of the first living body when the maximum value of the plurality of correlation coefficients is below the threshold.

Furthermore, for example, the circuit identifies the first living body and the second living body corresponding to a correlation coefficient having the maximum value as identical.

Furthermore, for example, the circuit may remove by a predetermined method a direct current (DC) component from at least the first reception signal among the first reception signal and the second reception signals.

Thus, it is possible to suppress the DC components, which are noise components unnecessary for biometric identification, in the reception signal, enabling efficient biometric identification.

Furthermore, for example, the circuit may calculate, as the plurality of correlation coefficients, a plurality of correlation coefficients between the teacher signals and the M×N first reception signals through the sliding correlation operation.

Accordingly, whether to perform the biometric authentication can be determined using the maximum value of time correlation coefficients of sliding correlation. Therefore, it is possible to reduce the occurrences of erroneous acceptance of a different person as a subject him or herself when the first living body is not included in the teacher data, enabling a reduction in the equal error rate (EER).

Furthermore, for example, the teacher signals may be the M×N second reception signals obtained as a result of the N receivers receiving, in advance, the second reception signals during a period that is K times longer than the predetermined period, K being at least 2.

Note that these general and specific aspects may be implemented using a system, a method, an integrated circuit, a computer program, or a computer-readable recording medium such as a compact disc read-only memory (CD-ROM), or any combination of systems, methods, integrated circuits, computer programs, or recording media.

Hereinafter, an embodiment of the present disclosure will be described in detail with reference to the drawings. Note that the embodiment described below presents a specific preferred example of the present disclosure. The numerical values, shapes, materials, structural elements, the arrangement and connection of the structural elements, steps, the processing order of the steps, etc., presented in the following embodiment are mere examples, and therefore do not limit the present disclosure. As such, among the structural elements in the following embodiment, structural elements not recited in any one of the independent claims which indicate the broadest concepts of the present disclosure are described as arbitrary structural elements of a preferred embodiment. In this Description and the drawings, structural elements having substantially identical functions or structures are assigned the same reference signs, and overlapping description thereof is omitted.

EMBODIMENT

[Structure of Identification Device 10]

Figure 2:
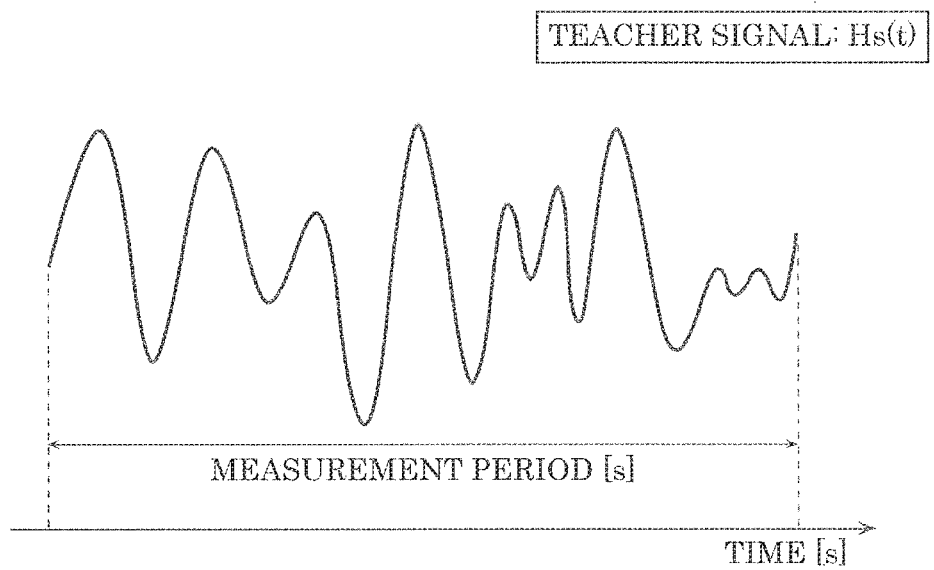
FIG. 2 illustrates an example of the teacher signal indicated in FIG. 1.
Figure 3:
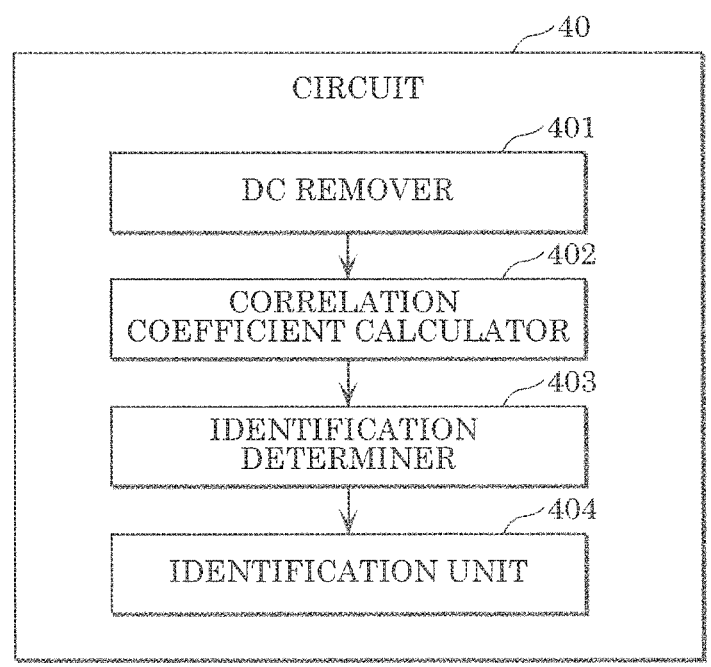
FIG. 3 is a configuration diagram illustrating an example of the detailed configuration of the circuit illustrated in FIG. 1.

FIG. 1 is a configuration diagram illustrating an example of the configuration of identification device 10 according to an embodiment. FIG. 2 illustrates an example of teacher signal 42 indicated in FIG. 1. FIG. 3 is a configuration diagram illustrating an example of the detailed configuration of circuit 40 illustrated in FIG. 1.

Identification device 10 according to the present disclosure includes: M transmission antenna elements (M is an integer greater than or equal to 1); N receivers (N is an integer greater than or equal to 3) each including a reception antenna element; circuit 40; and memory 41.

The M transmission antenna elements transmit transmission signals to predetermined area A1 including living body 50. The transmission signals are high frequency signals such as microwaves generated by a transmitter or the like. Living body 50 is a person, etc. Living body 50 is a subject to be identified by identification device 10 and is subject to biometric authentication. Predetermined area A1 is a space in a predetermined range which includes living body 50. In other words, predetermined area A1 is a space to be used by identification device 10 to identify living body 50.

For example, the M transmission antenna elements transmit first transmission signals to predetermined area A1 including a first living body which is living body 50 serving as a measurement target. Furthermore, the M transmission antenna elements transmit second transmission signals to predetermined area A1 including a second living body which is already-known living body 50 serving as teacher data.

The N receivers each include a reception antenna element and are disposed surrounding predetermined area A1. During a predetermined period, each of the N receivers receives, using the reception antenna element, a reception signal including a reflection signal obtained as a result of a transmission signal being reflected by living body 50. For example, during a predetermined period, each of the N receivers receives, using the reception antenna element, a first reception signal including a reflection signal obtained as a result of the first transmission signal being reflected by the first living body. Furthermore, for example, during a period that is K times longer (K is at least 2) than the predetermined period, each of the N receivers receives, using the reception antenna element, a teacher signal which is a second reception signal including a reflection signal obtained as a result of the second transmission signal being reflected by the second living body.

In the present embodiment, identification device 10 includes, for example, eight transmitters and receivers 30A to 30H, circuit 40, and memory 41, as illustrated in FIG. 1.

In other words, the M transmission antenna elements and the N receivers may be eight transmitters and receivers 30A to 30H. Note that the number of transmitters and receivers is not limited to eight.

[Transmitters and Receivers 30A to 30H]

In the present embodiment, eight transmitters and receivers 30A to 30H are disposed in positions surrounding predetermined area A1, and each transmit a transmission signal to predetermined area A1 including living body 50 such as a person, and receive a reception signal including a reflection signal obtained as a result of the transmission signal being reflected by living body 50. For example, eight transmitters and receivers 30A to 30H may be disposed at equal intervals in a circle and may be disposed in positions outside predetermined area A1.

As illustrated in FIG. 1, transmitters and receivers 30A to 30H includes antenna elements 31A to 31H, respectively. Transmitters and receivers 30A to 30H transmit transmission signals to predetermined area A1 using antenna elements 31A to 31H. More specifically, transmitters and receivers 30A to 30H emit microwaves as the transmission signals to living body 50 such as a person by antennal elements 31A to 31H. Note that using antenna elements 31A to 31H, transmitters and receivers 30A to 30H may transmit unmodulated transmission signals or may transmit modulated transmission signals. In the case of transmitting the modulated transmission signals, each of transmitters and receivers 30A to 30H may further include a circuit for performing a modulation process.

Furthermore, during a predetermined period, transmitters and receivers 30A to 30H receive, using antenna elements 31A to 31H, reception signals including reflection signals obtained as a result of the transmission signals being reflected by living body 50. Transmitters and receivers 30A to 30H output the received reception signals to circuit 40. Note that each of transmitters and receivers 30A to 30H may include a circuit for processing the reception signal. In this case, each of transmitters and receivers 30A to 30H may convert the received reception signal into a low frequency signal by applying a frequency transform to the received reception signal. Furthermore, each of transmitters and receivers 30A to 30H may perform demodulation on the reception signal. Subsequently, each of transmitters and receivers 30A to 30H outputs, to circuit 40, a signal obtained as a result of the frequency transform and/or the demodulation.

Note that in the example illustrated in FIG. 1, the transmitters and receivers are eight transmitters and receivers 30A to 30H each including a single antenna element used for both transmission and reception, but this is not limiting. The number of transmitters and receivers 30A to 30H is not limited to eight; N transmitters and receivers (N is an integer greater or equal to 3) may be used. Furthermore, a transmitter including M transmission antenna elements (M is an integer greater than or equal to 1) and a receiver including N reception antenna elements may be separately provided.

[Memory 41]

Memory 41 is an auxiliary storage device including a non-volatile storage area and is, for example, a read only memory (ROM), a flash memory, a hard disk drive (HDD), or the like. For example, memory 41 stores information to be used for various processes of operating identification device 10.

As illustrated in FIG. 1, memory 41 stores teacher signal 42. Teacher signal 42 has a signal waveform obtained in advance about the second living body which is already-known living body 50 present in predetermined area A1.

More specifically, teacher signal 42 is M×N second reception signals obtained as a result of the N receivers receiving, in advance, the second reception signals including reflection signals obtained as a result of the second transmission signals being transmitted from the M transmission antenna elements to the second living body and reflected by the second living body. Teacher signal 42 may be M×N second reception signals obtained as a result of the N receivers receiving, in advance, the second reception signals during a period that is K times longer (K is at least 2) than the predetermined period.

In the present embodiment, the M transmission antenna elements and the N receivers are eight transmitters and receivers 30A to 30H, as illustrated in FIG. 1. An example of teacher signal 42 in this case will be described with reference to FIG. 2. Teacher signal 42 illustrated in FIG. 2 is an example of the reception signal received by one receiver during a measurement period.

Teacher signal 42 illustrated in FIG. 2 has a time response waveform corresponding to a plurality of reception signals obtained as a result of transmitters and receivers 30A to 30H receiving, in advance, reception signals including reflection signals obtained as a result of the transmission signals being transmitted from antenna elements 31A to 31H to already-known living body 50 (the second living body) present in predetermined area A1 and then reflected off a surface of living body 50. Thus, teacher signal 42 illustrated in FIG. 2 is a plurality of reception signals obtained as a result of transmitters and receivers 30A to 30H receiving, in advance, reception signals including reflection signals during a measurement period. The measurement period is K times longer (K is at least 2) than the aforementioned predetermined period. The measurement period is, for example, 120 [s], but this is not limiting. The measurement period may be 3 [s], 10 [s], or 30 [s] as long as it is greater than or equal to the heartbeat period of the person.

Note that teacher signal 42 may be obtained in advance about each of a plurality of second living bodies already known. In this case, it is sufficient that a plurality of teacher signals 42 which are in one-to-one correspondence with the plurality of second living bodies already known be stored in memory 41, each in association with identification information for identifying the second living body corresponding thereto.

[Circuit 40]

Circuit 40 performs various processes of operating identification device 10. Circuit 40 includes, for example, a processor which executes a control program and a volatile storage area (main storage device) used as a work area for executing the control program. This storage area is, for example, a random access memory (RAM).

The first reception signal obtained from each of the N receivers is stored in the storage area of circuit 40 for a predetermined temporary period. The phase and amplitude of the first reception signal may be stored in the storage area of circuit 40 for a predetermined temporary period. In the present embodiment, the reception signal obtained from each of transmitters and receivers 30A to 30H is stored in the storage area of circuit 40 for a predetermined temporary period.

Note that circuit 40 may be formed of a dedicated circuit for performing various processes of operating identification device 10. Specifically, circuit 40 may be a circuit that performs a software process or may be a circuit that performs a hardware process. Furthermore, circuit 40 may include a non-volatile storage area.

Next, the functional configuration of circuit 40 will be described.

As illustrated in FIG. 3, circuit 40 includes DC remover 401, correlation coefficient calculator 402, identification determiner 403, and identification unit 404. Note that DC remover 401 is not necessarily indispensable.

<DC Remover 401>

DC remover 401 removes, by a predetermined method, a direct current (DC) component from at least the first reception signal among the first reception signal and the second reception signal.

More specifically, first, DC remover 401 calculates each propagation channel H(t) using the reception signal stored in the storage area of circuit 40 and the teacher signal stored in memory 41.

Expression 1 below represents propagation channel H(t) obtained when a multiple-input and multiple-output (MIMO) array antenna including $M_r$ reception antenna elements and $M_t$ transmission antenna elements are disposed around living body 50.

[Math. 1]

$$H(t) = \begin{pmatrix} h_{11}(t) & \cdots & h_{1M_t}(t) \\ \vdots & \ddots & \vdots \\ h_{M_r1}(t) & \cdots & h_{M_rN_t}(t) \end{pmatrix} \quad \text{(Expression 1)}$$

In Expression 1, $h_{ij}$ represents a complex channel response of the j-th transmitter to the i-th receiver, and t represents observation time.

Next, DC remover 401 calculates a DC-removed channel, represented in Expression 2 below, which is a propagation channel for each of the reception signal and the teacher signal from which DC components, which are noise components unnecessary for identification of living body 50, has been removed. DC remover 401 may store the calculated DC-removed channel in memory 41 or may store the calculated DC-removed channel in the storage area of circuit 40.

DC-removed channel $H_{w/o\ DC}(t)$ of each of the reception signal and the teacher signal is calculated by subtracting, from each component of the propagation channel, a DC component calculated by the average measurement time of the component, as represented in Expressions 3 and 4 below.

[Math. 2]

$$H_{w/o}(t) = \begin{pmatrix} h_{e11}(t) & \cdots & h_{e1M_t}(t) \\ \vdots & \ddots & \vdots \\ h_{eM_r1}(t) & \cdots & h_{eM_rM_t}(t) \end{pmatrix} \quad \text{(Expression 2)}$$

[Math. 3]

$$H_{w/oDCij}(t) = h_{ij}(t) - \sum_{k=j}^{N-1} h_{ij}(k)/N \quad \text{(Expression 3)}$$

[Math. 4]

$$N = F_s \cdot T \quad \text{(Expression 4)}$$

Here, N represents the number of snapshots, $F_s$ represents a sampling frequency, and T represents measurement time.

Note that the method for removing DC components is not limited to the method represent in the right-hand side of Expression 3. For example, DC components may be removed by subtracting a propagation channel obtained in predetermined unoccupied area A1 where living body 50 is absent.

<Correlation Coefficient Calculator 402>

Correlation coefficient calculator 402 calculates a plurality of correlation coefficients by comparing teacher signal 42 stored in memory 41 and the plurality of reception signals stored in the storage area of circuit 40. More specifically, correlation coefficient calculator 402 calculates a plurality of correlation coefficients from the teacher signal and M×N first reception signals obtained as a result of each of the N receivers receiving the first reception signal.

The plurality of correlation coefficients may be calculated through the sliding correlation operation. Specifically, correlation coefficient calculator 402 may calculate, as said plurality of coefficients, a plurality of coefficients between the teacher signal and respective ones of the M×N first reception signals through the sliding correlation operation. Note that the sliding correlation operation is a calculation in which, while being slid, the observed reception signal is compared with the teacher signal so that a time relationship where the two signals have the highest correlation can be found.

Furthermore, when DC remover 401 calculates the DC-removed channels of the plurality of reception signals and teach signal 42 and stores the DC-removed channels in memory 41 or the storage space of circuit 40, correlation coefficient calculator 402 may calculate the plurality of correlation coefficients using the DC-removed channels of the plurality of reception signals and teacher signal 42. The plurality of correlation coefficients may be calculated through the sliding correlation operation. Stated differently, correlation coefficient calculator 402 may calculate the plurality of correlation coefficients between teacher signal 42 and the plurality of reception signals using the DC-removed channels thereof through the sliding correlation operation.

Here, an example of the method for calculating the plurality of correlation coefficients will be described.

A measurement channel obtained about predetermined region A1 including the first living body using Expression 1 where the number of snapshots is referred to as $N_T$ is referred to as identification channel $H_T(t)$. Furthermore, the database channel of the q-th registrant previously subjected to the measurement using Expression 1 in the same way where the number of registrants is referred to as S and the number of snapshots is referred to as $N_D$ is referred to as HD(t, q). Note that $H_D(t, q)$ corresponds to a measurement channel obtained about predetermined area A1 including the second living body that is the q-th living body in the teacher signal.

Here, in order to shorten the measurement time for obtaining the identification channel, the number of snapshots $N_T$ and the number of snapshots $N_D$ are set to have the relationship indicated in Expression 5. The length of the time window of the sliding correlation is referred to as $N_T$.

[Math. 5]

$$N_T < N_D \qquad \text{(Expression 5)}$$

The identification channel and the database channel which have the same time window and from which the DC components have been removed using Expression 2 are referred to as $H_{TW/o\,DC}(t)$ and $H_{DW/oDC}(t, q)$. Using these, evaluation function ρ(p, q) involving the sliding correlation is calculated by an operation for determining the correlation coefficients which is represented by Expressions 6 and 7. In Expressions 6 and 7, p represent the number of loops for calculating the sliding correlation.

[Math. 6]

$$\rho(p, q) = \frac{\left| \sum_{k=0}^{N_T-1} \sum_{j=1}^{M_t} \sum_{i=1}^{M_r} H_{TwlcDC}(k/F_c) Hd^H\left(\frac{k}{F_s}, q\right) \right|}{\sqrt{\sum_{k=0}^{N_T-1} \sum_{j=1}^{M_t} \sum_{i=1}^{M_r} \left|H_{TwloDC}(k/F_s)\right|^2 \sum_{k=0}^{N_T-1} \sum_{j=1}^{M_t} \sum_{i=1}^{M_r} \left|Hd\left(\frac{k}{F_s}, q\right)\right|^2}} \qquad \text{(Expression 6)}$$

[Math. 7]

$$Hd(t, q) = H_{\frac{Dw}{oDC}}\left(t + \frac{p-1}{F_s}, q\right), \qquad \text{(Expression 7)}$$
$$(p = 1, 2, \ldots, N_D - N_T + 1, q = 1, 2, \ldots, S) S_l(t) = [S_{l1}(t), \ldots, S_{lM}(t)]$$

Note that evaluation function ρ(p, q) involving the sliding correlation is not limited to that represented by Expressions 6 and 7 stated above and may be represented, for example, by Expression 8. Furthermore, evaluation function ρ(p, q) involving the sliding correlation may be represented by Expression 9 or 10 obtained by excluding the number of trials r from Expression 8. In Expression 9, the correlation is calculated using the expected value of time correlation. In Expression 10, the correlation of a combination of antennas having the highest time correlation is calculated; in other words, a combination having high correlation is selected from among MIMO combinations to calculate the correlation.

[Math. 8]

$$\rho(p, q) = \frac{\left|\sum_{k=0}^{N_T-1} \sum_{j=1}^{M_t} \sum_{i=1}^{M_r} H_{Te}\left(\frac{k}{F_s}\right) H_{De}^H\left(\frac{k+p}{F_s}, q\right)\right|}{\sqrt{\left|\sum_{k=0}^{N_T-1} \sum_{j=1}^{M_t} \sum_{i=1}^{M_r} \left|H_{Te}\left(\frac{k}{F_s}\right)\right|^2 \sum_{k=0}^{N_T-1} \sum_{j=1}^{M_t} \sum_{i=1}^{M_r} H_{De}\left(\frac{k+p}{F_s}, q\right)\right|^2}}$$

(Expression 8)

[Math. 9]

$$\rho(p, q) = \frac{\sum_{k=0}^{N_T-1} \left|H_{Te}\left(\frac{k}{F_s}\right) H_{De}^H\left(\frac{k+D}{F_s}, q\right)\right|}{\sqrt{\sum_{j=1}^{M_t} \sum_{i=1}^{M_r} \left|\sum_{k=0}^{N_T-1} H_{Te}\left(\frac{k}{F_s}\right)\right|^2 \sum_{j=1}^{M_t} \sum_{i=1}^{M_r} \left|\sum_{k=0}^{N_T-1} H_{De}\left(\frac{k+p}{F_s}, q\right)\right|^2}}$$

(Expression 9)

[Math. 10]

$$\rho(p, q) = \frac{\left|\sum_{k=0}^{N_T-1} \max\left(H_{Te}\left(\frac{k}{F_s}\right) H_{De}^H\left(\frac{k+p}{F_s}, q\right)\right)\right|}{N_t}$$

(Expression 10)

<Identification Determiner 403>

Identification determiner 403 determines whether or not the maximum value of the plurality of correlation coefficients calculated exceeds the threshold, and identification unit 404 performs biometric authentication of the first living body accordingly. For example, identification determiner 403 may determine that when the maximum value of the plurality of correlation coefficients calculated exceeds the threshold, the biometric authentication of the first living body is to be performed, and when the maximum value of the plurality of correlation coefficients is below the threshold, the biometric authentication of the first living body is not to be performed.

In the present embodiment, identification determiner 403 compares the maximum value of the plurality of correlation coefficients calculated by correlation coefficient calculator 402 and the threshold input by a predetermined method, for example, 0.6. For example, when identification determiner 403 determines that the maximum value of the correlation coefficients is greater than or equal to the threshold, identification unit 404 performs, as the biometric authentication of the first living body, the process of identifying the first living body. On the other hand, when the maximum value of the correlation coefficients is less than the threshold, identification determiner 403 determines that the teacher signal does not include the data of the first living body, and the identification process ends without the biometric authentication of the first living body being performed. For example, identification determiner 403 compares the threshold and maximum evaluation function $\rho_{max}$ (p, q) extracted from evaluation function $\rho(p, q)$ represented in Expression 6, and the biometric authentication of the first living body is performed according to whether or not the maximum evaluation function $\rho_{max}$ (p, q) exceeds the threshold.

<Identification Unit 404>

When the biometric authentication of the first living body is to be performed, identification unit 404 identifies by a predetermined method the first living body and the second living body as identical. More specifically, identification unit 404 identifies, as the same living body, the first living body and the second living body corresponding to a correlation coefficient having the maximum value.

In the present embodiment, when identification determiner 403 determines that the maximum value of the correlation coefficients is greater than or equal to the threshold, identification unit 404 identifies living body 50 from which the maximum value of the correlation coefficients has been obtained as identical to already-known living body 50 included in the teacher data. Specifically, identification unit 404 classifies, as the first living body subject to the biometric authentication, registrant q (the second living body) from which maximum evaluation function $\rho_{max}$(p, q) extracted has been obtained, thereby identifying registrant q as identical to the first living body.

In this way, identification device 10 illustrated in FIG. 1 can identify living body 50 by processing, in circuit 40, the reception signals received by transmitters and receivers 30A to 30H.

[Operations of Identification Device 10]

Figure 4:
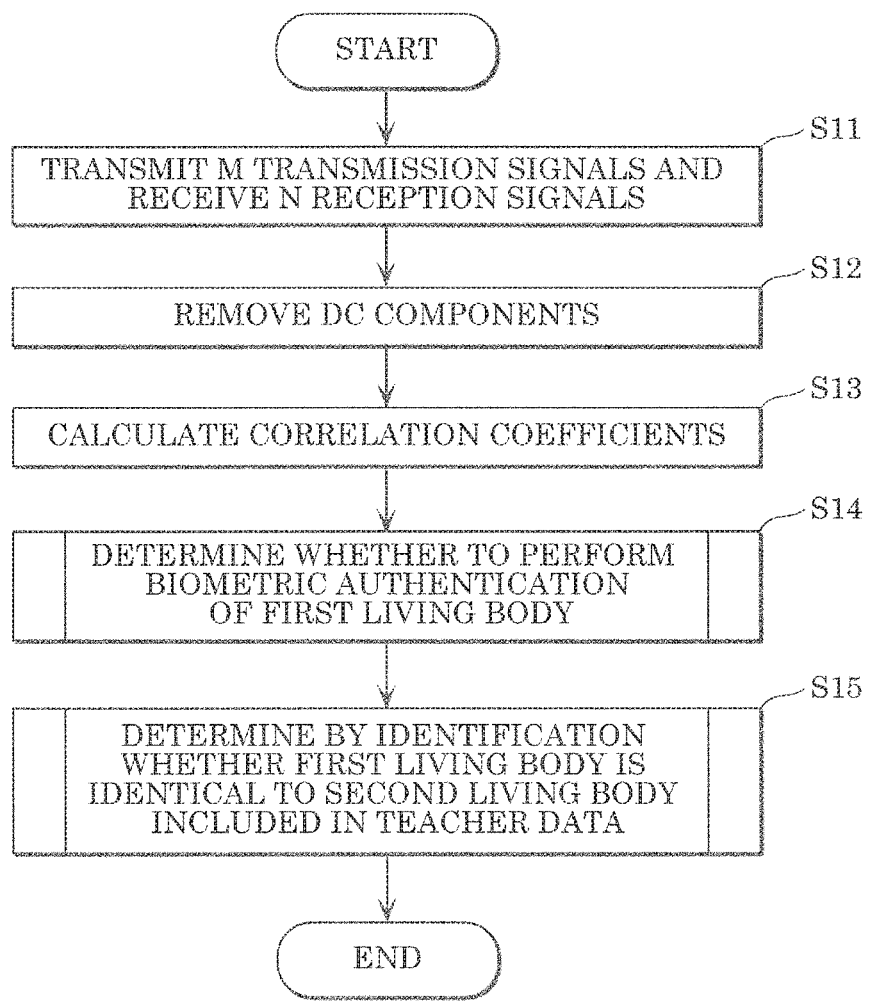
FIG. 4 is a flowchart illustrating an example of the operations of an identification device according to an embodiment.
Figure 5:
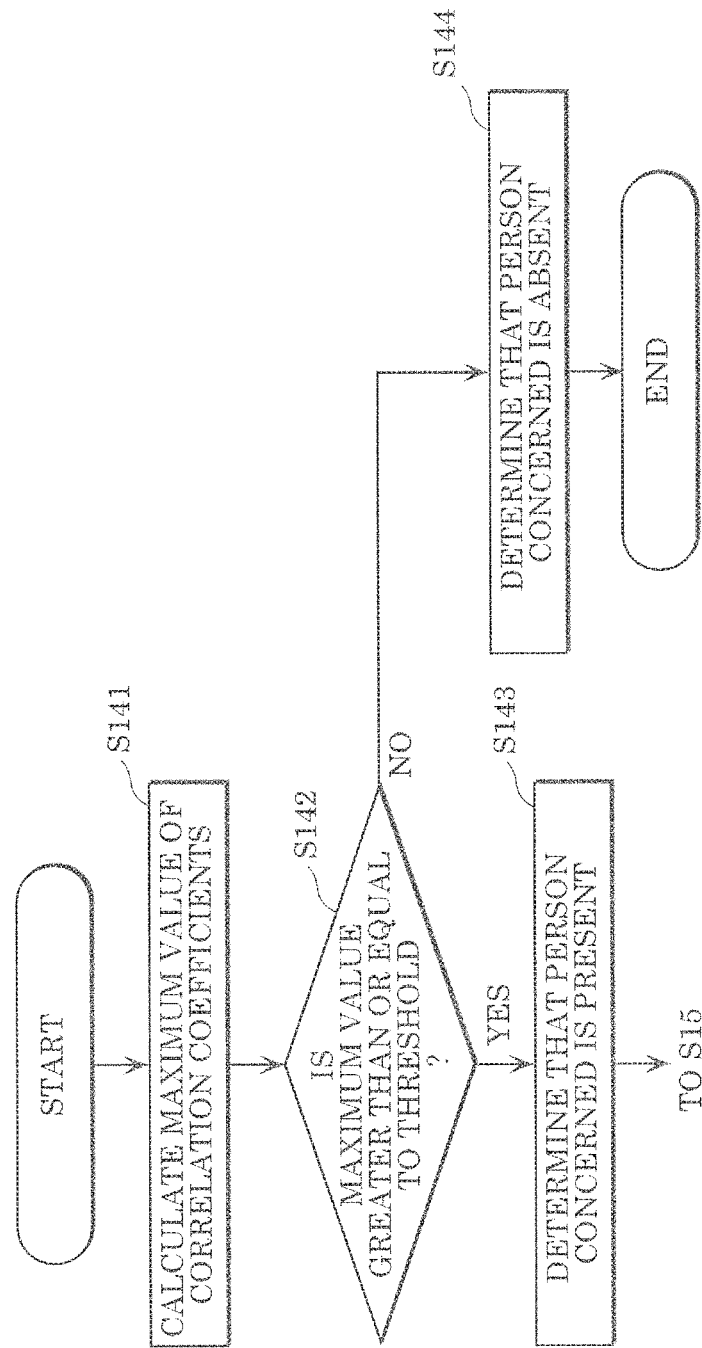
FIG. 5 is a flowchart illustrating the detailed operation in Step S14 indicated in FIG. 4.
Figure 6:
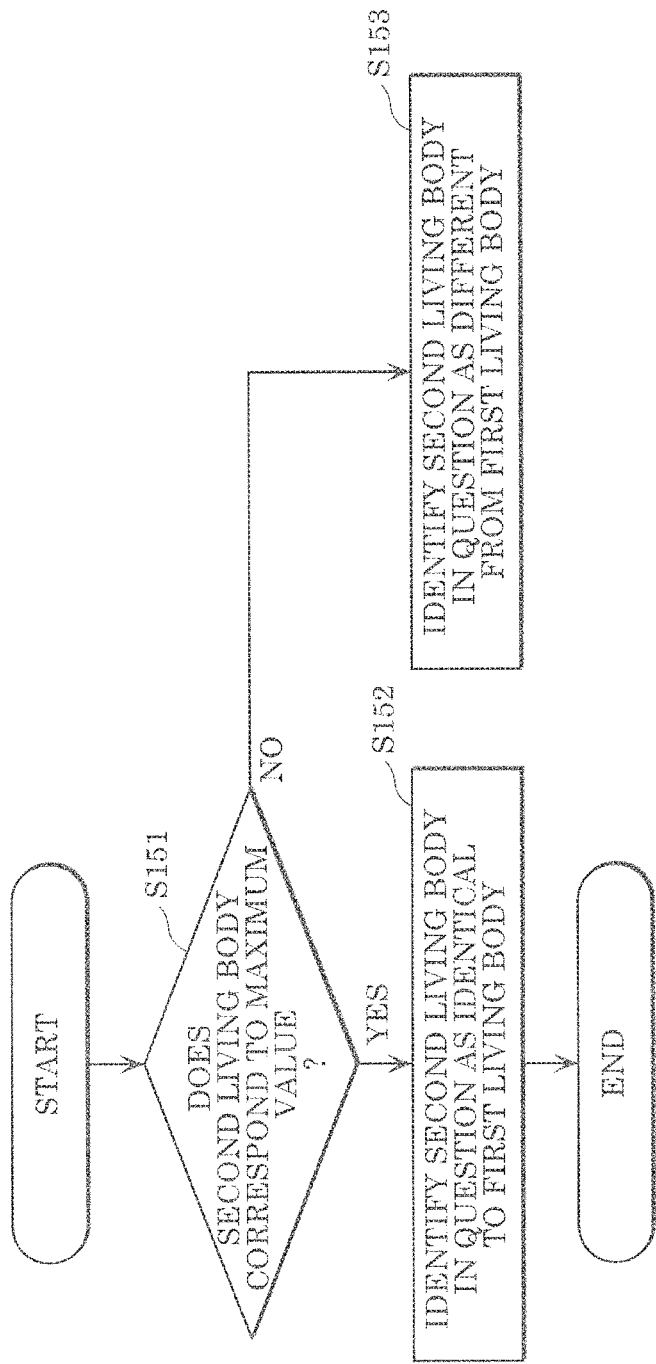
FIG. 6 is a flowchart illustrating the detailed operation in Step S15 indicated in FIG. 4.

Next, operations of identification device 10 configured as described above will be described. FIG. 4 is a flowchart illustrating an example of the operations of identification device 10 according to the embodiment. FIG. 5 is a flowchart illustrating the detailed operation in Step S14 indicated in FIG. 4. FIG. 6 is a flowchart illustrating the detailed operation in Step S15 indicated in FIG. 4.

First, identification device 10 transmits M transmission signals and receives N reception signals (S11). More specifically, using the M transmission antenna elements, identification device 10 transmits the first transmission signals to predetermined area A1 including the first living body. Subsequently, in identification device 10, during the predetermined period, the N respective receivers receive, using the reception antenna elements, the first reception signals including reflection signals obtained as a result of the first transmission signals being reflected by the first living body. In the present embodiment, transmitters and receivers 30A to 30H cause antennal elements 31A to 31H to transmit the transmission signals to predetermined area A1 in the state where the first living body which is living body 50 to be identified is disposed within predetermined area A1. Subsequently, during the predetermined period, transmitter and receivers 30A to 30H receive, using antenna elements 31A to 31H, the first reception signals including reflection signals obtained as a result of the first transmission signals being reflected by the first living body.

Figure 7:
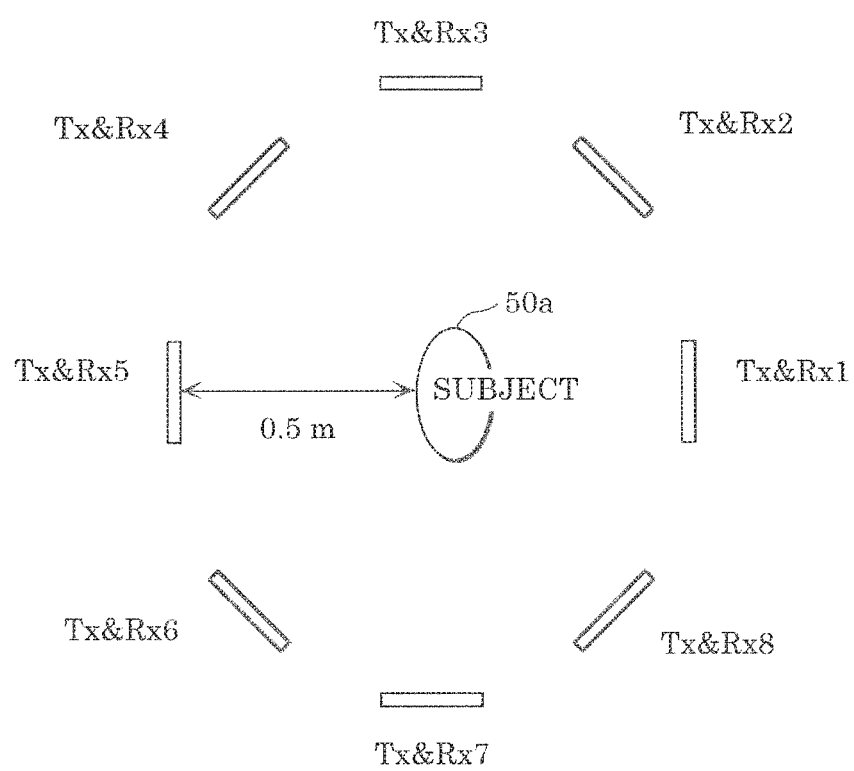
FIG. 7 illustrates an environment in which an identification test using an identification device according to an embodiment is performed.
Figure 8:
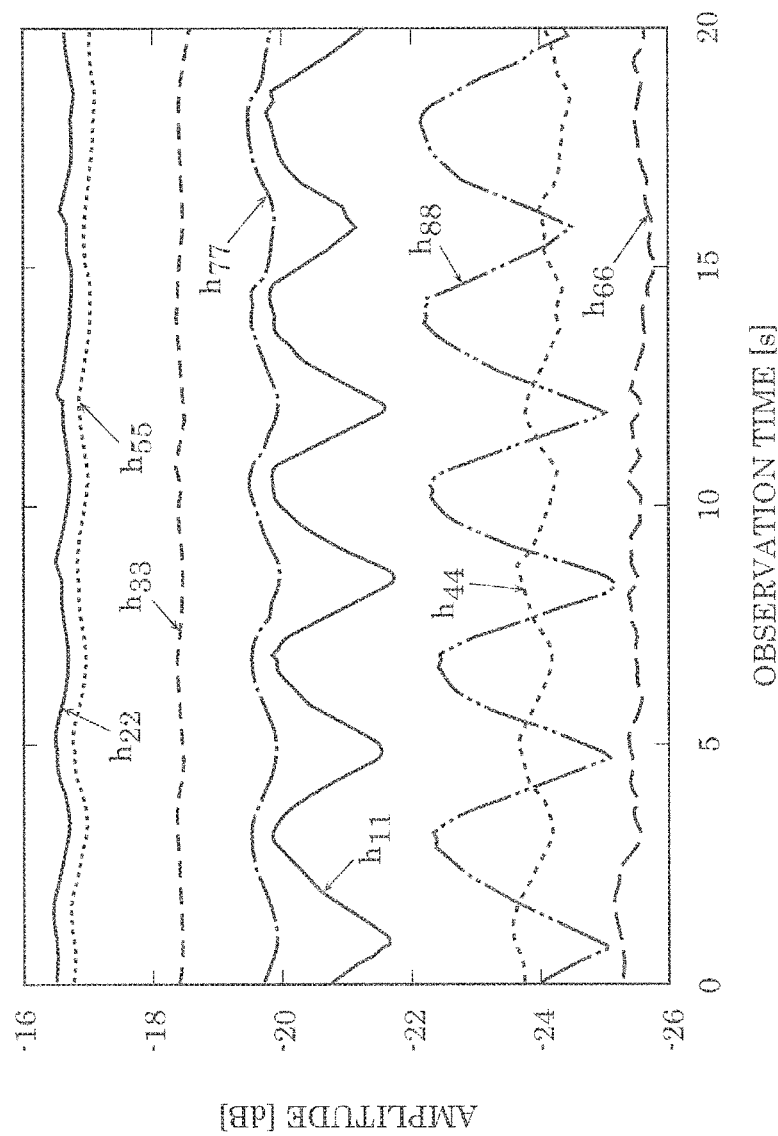
FIG. 8 illustrates an example of propagation channels calculated from reception signals received in the environment illustrated in FIG. 7.

FIG. 7 illustrates an environment in which an identification test using identification device 10 according to the embodiment is performed. FIG. 8 illustrates an example of propagation channels calculated from reception signals received in the environment illustrated in FIG. 7.

As illustrated in FIG. 7, in the present identification test, eight transmitters and receivers equivalent to transmitters and receivers 30A to 30H are used. The eight transmitters and receivers are arranged at 45-degree intervals in a circle centered on subject 50a and having a radius of 0.5 m. Subject 50a corresponds to living body 50 to be identified in the identification test, that is, the first living body. Single-element square patch antennas are used as the reception antenna elements and the transmission antenna elements corresponding to antenna elements 31A to 31H. More specifically, each of the eight reception antenna elements of the eight transmitters and receivers is a square patch antenna and is installed at a level of 0.9 m from a floor surface. The eight transmission antenna elements of the eight transmitters and receivers are provided right above the corresponding reception antenna elements by one wavelength of microwaves.

As can be seen from FIG. 8, component $h_{11}$ and component $h_{88}$ of the propagation channels exhibit periodic, wide variations with similar waveforms compared to other components. Component $h_{11}$ is a channel response from the reception antenna element located in front of subject 50a, and component $h_{88}$ is a channel response from the reception antenna element located forward of subject 50a on the right-hand side.

The other components are channel responses from the reception antenna elements located on the back or side surface of subject 50a. In other words, this shows that variations on the back and side surfaces of the living body are small. This is considered to be due to the fact that variations attributed to activities of a living body occur in the chest and/or abdomen of the living body.

Next, identification device 10 removes DC components from the plurality of reception signals obtained in Step S11 and teacher signals 42 stored in memory 41 (S12). More specifically, first, identification device 10 reads, from memory 41, teacher signals 42 which are the M×N second reception signals obtained as a result of the N receivers receiving, in advance, reflection signals obtained as a result of the second transmission signals being transmitted from the M transmission antenna elements to the second living body, which is already-known living body 50, and then reflected by the second body. Subsequently, identification device 10 removes DC components from the first reception signals obtained in Step S11 and teacher signals 42 read from memory 41. In the present embodiment, circuit 40 reads teacher signals 42 from memory 41 and, using teacher signals 42 and the reception signals obtained in Step S11, calculates the DC-removed channel of each of these signals.

Figure 9:
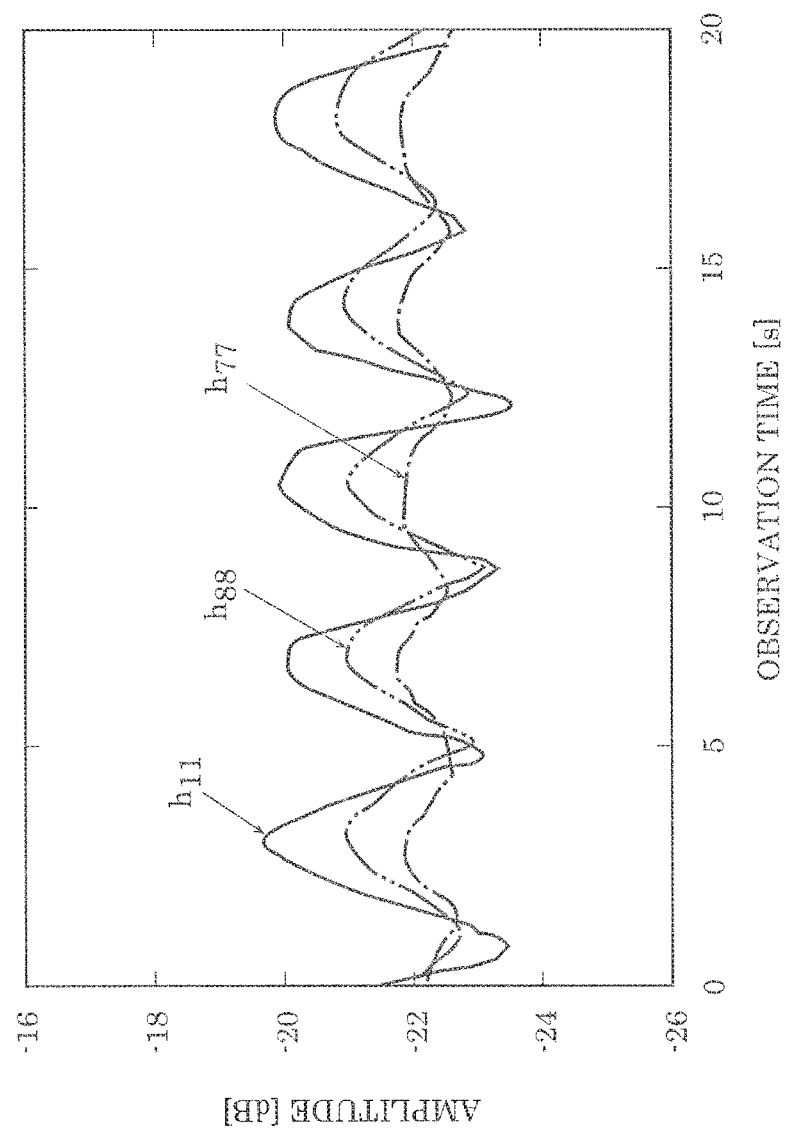
FIG. 9 illustrates an example of DC-removed channels which are the propagation channels illustrated in FIG. 8 from which direct-current (DC) components have been removed.

FIG. 9 illustrates an example of DC-removed channels which are the propagation channels illustrated in FIG. 8 from which DC components have been removed. In FIG. 9, components $h_{11}$, $h_{88}$, and $h_{77}$ of DC-removed channels which are propagation channels from which DC components have been removed from components $h_{11}$, $h_{88}$, and $h_{77}$ are illustrated as an example. As illustrated in FIG. 8, since the DC components of the propagation channels are different depending on the position on subject 50a, the position of the waveform of the components of the propagation channels along the vertical axis (indicating the strength) is different. If the identification process is performed using the components of propagation channels having such different DC components, the accuracy of identification decreases. In contrast, in FIG. 9 where the DC components of the propagation channels have been removed, the positions of the waveforms of the components of the propagation channels along the vertical axis (indicating the strength) match each other. In other words, when the identification process is performed using the components of propagation channels from which DC components have been removed, the accuracy of identification improves.

Next, identification device 10 calculates a plurality of correlation coefficients using teacher signals 42 and the plurality of reception signals from which the DC components have been removed in Step S12 (S13). More specifically, identification device 10 calculates a plurality of correlation coefficients from the teacher signals from which the DC components have been removed by a predetermined method and the M×N first reception signals which have been received by the respective N receivers and from which the DC components have been removed by a predetermined method. In the present embodiment, circuit 40 calculates a plurality of correlation coefficients from the respective DC-removed channels calculated in Step S12. Note that the details of the method for calculating the plurality of correlation coefficients are as described above using Expressions 1 to 10, and as such, description thereof will be omitted.

Next, identification device 10 determines whether or not to perform the biometric authentication of the first living body (S14). Specifically, identification device 10 determines whether or not to perform the biometric authentication of the first living body according to whether or not the maximum value of the plurality of correlation coefficients exceeds the threshold.

More specifically, as illustrated in FIG. 5, first, circuit 40 calculates the maximum value of the plurality of correlation coefficients calculated in Step S13 (S141). Subsequently, circuit 40 compares the maximum value of the correlation coefficients and the threshold, for example, 0.6, thereby determining whether or not the maximum value of the correlation coefficients is greater than or equal to the threshold (S142). When the maximum value of the correlation coefficient is greater than or equal to the threshold in Step S142 (YES in S142), circuit 40 determines that a person concerned is present (S143), and the processing proceeds to Step S15. On the other hand, when the maximum value of the correlation coefficients is less than the threshold in Step S142 (NO in Step S144), circuit 40 determines that the person concerned is absent (S144), and ends the operation of identification device 10. Note that when determining that the person concerned is absent, identification device 10 may determine that living body 50 to be identified, that is, the first living body, is not already-known living body 50 included in the teacher signals, and may return a response rejecting the biometric authentication.

Figure 10:
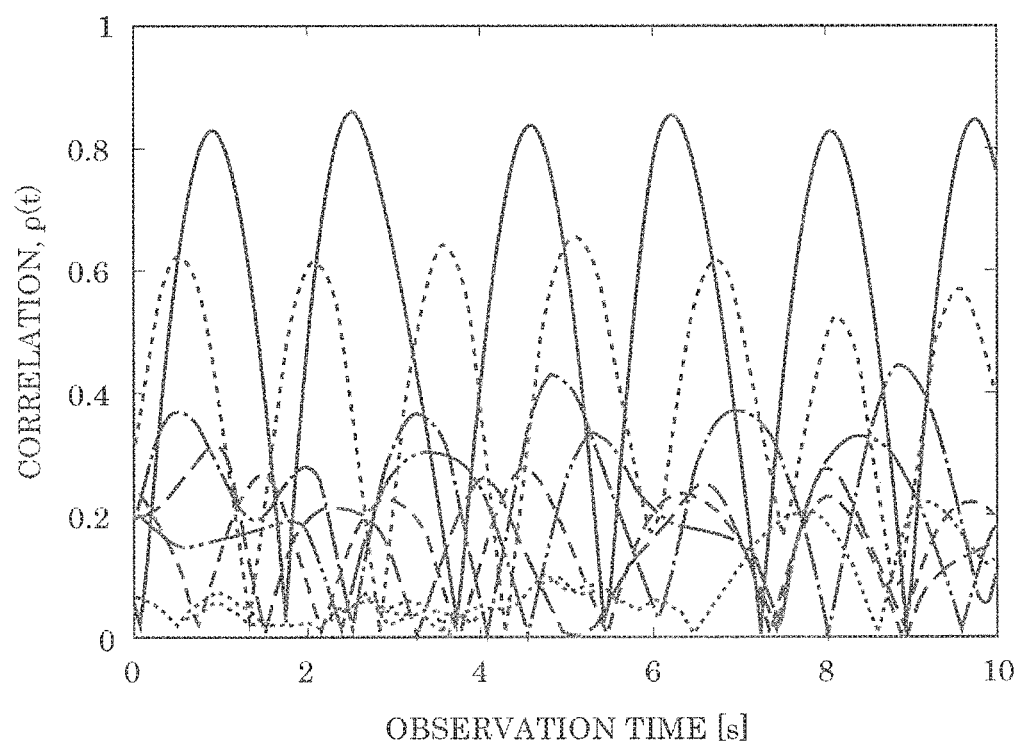
FIG. 10 illustrates an example of a graph in which more than one maximum value of the correlation coefficients is included.

FIG. 10 illustrates an example of a graph in which more than one maximum value of the correlation coefficients is included. FIG. 10 exemplifies maximum evaluation function $\rho_{max}$ (p, q) of evaluation function $\rho(p, q)$ involving the sliding correlation, represented in Expression 6, for example. FIG. 10 illustrates the sliding correlation between the plurality of second living bodies included in the teacher data and the first living body which is living body 50 to be identified. In FIG. 10, the correlation coefficient shown by the solid line having the highest peak indicates that there is the second living body matching the first living body. The correlation coefficient shown by the dashed line having the second highest peak indicates that there is the second living body having characteristics very similar to those of the first living body. The correlation coefficients shown by lines having the third and following peaks indicate that there are the second living bodies which are other persons having characteristics different from those of the first living body.

Figure 11:
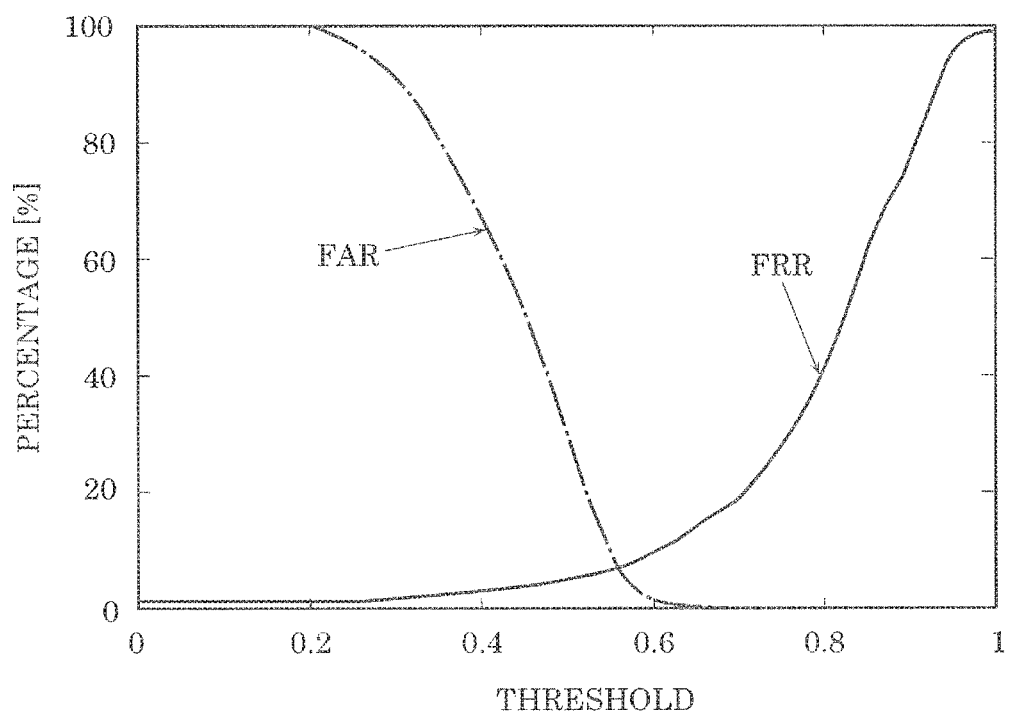
FIG. 11 illustrates FAR and FRR plotted with variable thresholds in an embodiment.

FIG. 11 illustrates FAR and FRR plotted with variable thresholds in the embodiment. FIG. 11 shows the false rejection rate (FRR) and the false acceptance rate (FAR) obtained when the biometric authentication is performed using a changing threshold and the plurality of correlation coefficients calculated by identification device 10. As illustrated in FIG. 11, as the threshold increases, the false acceptance rate (FAR) decreases and at the same time, the false rejection rate (FRR) increases. In other words, FIG. 11 shows that when the threshold is set large, for example, 0.7, instead of 0.6, the false acceptance rate (FAR) decreases further, but the false rejection rate (FRR) increases. Although the threshold is set to 0.6 in the present embodiment, this threshold may be changed, as appropriate, according to requirements to be applied.

Next, identification device 10 identifies whether or not the first living body is identical to the second living body included in the teacher data (S15). Specifically, in the case of performing the biometric authentication of the first living body, identification device 10 identifies by a predetermined method the first living body and the second living body as identical.

More specifically, as illustrated in FIG. 6, first, circuit 40 determines whether the second living body to be used for identifying whether to be identical to the first living body is the second living body corresponding to the maximum value of the correlation coefficients among the second living bodies included in the teacher data (S151). When determining that the second living body in question is the second living body corresponding to the maximum value of the correlation coefficients in Step S151 (YES in S151), circuit 40 identifies the second living body in question as identical to the first living body to be identified for the biometric authentication (S152), and ends the biometric authentication of the first living body. On the other hand when determining that the second living body in question is not the second living body corresponding to the maximum value of the correlation coefficients in Step S151 (NO in S151), circuit 40 identifies the second living body in question and the first living body to be identified for the biometric authentication as different (S153), and the processing returns to Step S151.

Advantageous Effects, Etc.

In the environment used in the identification test illustrated in FIG. 7, identification device 10 transmits a transmission wave from each of the antenna elements installed, for example, in eight locations around living body 50, and receives the reception signal. Subsequently, identification device 10 calculates, through the sliding correlation operation, a plurality of temporal correlations between the teacher signals stored in memory 41 and the reception signals from subject 50a which is living body 50 subject to the biometric authentication. When subject 50a and already-known living body 50 included in the teacher signals match, that is, when already-known living body 50 and subject 50a are the same person, the correlation coefficients in the sliding correlation have a large maximum value. On the other hand, when subject 50a and already-known living body 50 included in the teacher signals do not match, that is, when already-known living body 50 and subject 50a are different persons, the correlation coefficients in the sliding correlation have a small maximum value. Thus, using the maximum value of the correlation coefficients calculated through the sliding correlation operation, identification device 10 can determine whether or not data of subject 50a is present as the data of already-known living body 50 included in the teacher signals.

In addition, it has been found that this tendency becomes more apparent as a greater number of antenna elements are installed, which can contribute more to improvement of the equal error rate (EER).

A DC bias has been applied to the reception signal which is obtained by each of the antenna elements of identification device 10; this DC bias is susceptible to individual differences in identification device 10 and subtle differences in the position of living body 50 and has an impact on the identification rate. Therefore, identification device 10 according to the present embodiment calculates a plurality of correlation coefficients using the reception signals from which the DC components have been removed. This improves the identification rate.

As described above, with identification device 10 according to the present embodiment, the plurality of correlation coefficients can be calculated from the teacher signals and the first reception signals which are measurement signals obtained from the reception antenna elements installed around the first living body. Subsequently, according to whether the maximum value of the plurality of correlation coefficients exceeds the threshold, the first living body and the second living body included in the teacher data are identified as identical; in this way, the biometric authentication can be performed. Therefore, it is possible to reduce the occurrences of erroneous acceptance of a different person as a subject him or herself when the first living body is not included in the teacher data, enabling a reduction in the equal error rate (EER).

To use the example illustrated in FIG. 1, identification device 10 performs the biometric identification using the reception signals received by N transmitters and receivers 30A to 30H disposed surrounding predetermined area A1. Comparison is made to determine whether the maximum value of the correlation coefficients calculated before the biometric identification exceeds the threshold, and when the maximum value of the correlation coefficients is less than or equal to the threshold, it is determined that the person concerned is absent. Thus, it is possible to determine that the person concerned is absent when living body 50 subject to the biometric authentication, that is, the first living boy, is not present as already-known living body 50 included in the teacher data, that is, the second living body, enabling a reduction in the equal error rate (EER).

Furthermore, identification device 10 according to the present embodiment removes the DC components of the first reception signal and the second reception signal by the predetermined method before calculating the correlation coefficients. Thus, it is possible to reduce DC components, which are noise components unnecessary for biometric identification, in the reception signals; therefore, the biometric identification can be efficiently performed in a short time.

Furthermore, identification device 10 according to the present embodiment may calculate the plurality of correlation coefficients through the sliding correlation operation. Accordingly, whether to perform the biometric authentication can be determined using the maximum value of the time correlation coefficients of sliding correlation. Therefore, it is possible to reduce the occurrences of erroneous acceptance of a different person as a subject him or herself when the first living body is not included in the teacher data, enabling a reduction in the equal error rate (EER).

Furthermore, identification device 10 according to the present embodiment is capable of identifying living body 50, such as a person, using radio signals such as microwaves. Specifically, identification device 10 according to the present embodiment is capable of identifying living body 50, such as a person, without performing image analysis on an image captured by a camera or the like. Thus, a person can be identified in the state where the privacy of the person is protected.

Although only an exemplary embodiment of the present disclosure has been described in detail above, those skilled in the art will readily appreciate that many modifications are possible in the exemplary embodiment without materially departing from the novel teachings and advantages of the present disclosure. Accordingly, all such modifications are intended to be included within the scope of the present disclosure.

INDUSTRIAL APPLICABILITY

The present disclosure can be used in an identification device and method for identifying a living body using a radio signal, particularly, an identification device and method used for a home appliance that performs control according to a living body, a monitoring device that detects a living body who is trespassing, etc.

What is claimed is:

1. An identification device comprising:
M transmission antenna elements each of which transmits a first transmission signal to a predetermined area including a first living body, M being an integer greater than or equal to 1;
N receivers disposed surrounding the predetermined area, each of the N receivers including a reception antenna element and receiving a first reception signal using the reception antenna element during a predetermined period, N being an integer greater than or equal to 3, the first reception signal including a reflection signal obtained as a result of the first transmission signal being reflected by the first living body;
a memory in which teacher signals are stored, the teacher signals being M×N second reception signals obtained as a result of the N receivers receiving, in advance, second reception signals including reflection signals obtained as a result of second transmission signals being transmitted from the M transmission antenna elements to a second living body and reflected by the second living body; and
a circuit which calculates a plurality of correlation coefficients from the teacher signals and M×N first reception signals obtained as a result of each of the N receivers receiving the first reception signal, performs biometric authentication of the first living body according to whether or not a maximum value of the plurality of correlation coefficients calculated exceeds a threshold, and when the biometric authentication of the first living body is to be performed, identifies by a predetermined method the first living body and the second living body as identical, wherein the circuit removes by a predetermined method a direct current (DC) component from at least the first reception signal among the first reception signal and the second reception signals.

2. The identification device according to claim 1, wherein the circuit performs the biometric authentication of the first living body when the maximum value of the plurality of correlation coefficients calculated exceeds the threshold, and refrains from performing the biometric authentication of the first living body when the maximum value of the plurality of coefficients is below the threshold.

3. The identification device according to claim 1, wherein the circuit identifies the first living body and the second living body corresponding to a correlation coefficient having the maximum value as identical.

4. The identification device according to claim 1, wherein the circuit calculates, as the plurality of correlation coefficients, a plurality of correlation coefficients between the teacher signals and respective ones of the M.times.N first reception signals through a sliding correlation operation.

5. The identification device according to claim 1, wherein the teacher signals are the M.times.N second reception signals obtained as a result of the N receivers receiving, in advance, the second reception signals during a period that is K times longer than the predetermined period, K being at least 2.

6. An identification method used in an identification device including:
M transmission antenna elements, M being an integer greater than or equal to 1; N receivers disposed surrounding a predetermined area and each including a reception antenna element, N being an integer greater than or equal to 3; a memory; and a circuit, the identification method comprising:
transmitting, using the M transmission antenna elements, a first transmission signal to a predetermined area including a first living body;
receiving a first reception signal by each of the N receivers using the reception antenna element during a predetermined period, the first reception signal including a reflection signal obtained as a result of the first transmission signal being reflected by the first living body;
reading, from the memory, teacher signals which are M×N second reception signals obtained as a result of the N receivers receiving, in advance, second reception signals including reflection signals obtained as a result of second transmission signals being transmitted from the M transmission antenna elements to a second living body and reflected by the second living body;
calculating, by the circuit, a plurality of correlation coefficients from the teacher signals which have been read and M×N first reception signals obtained as a result of each of the N receivers receiving the first reception signal, wherein the circuit removes by a predetermined method a direct current (DC) component from at least the first reception signal among the first reception signal and the second reception signals;
performing biometric authentication of the first living body according to whether or not a maximum value of the plurality of correlation coefficients calculated exceeds a threshold; and
identifying by a predetermined method the first living body and the second living body as identical when the biometric authentication of the first living body is to be performed.

* * * * *